(12) United States Patent
Puzhevich et al.

(10) Patent No.: US 10,789,457 B2
(45) Date of Patent: Sep. 29, 2020

(54) SENSOR-BASED TRACKING OF SPORTS PARTICIPANTS

(71) Applicant: SAP SE, Walldorf (DE)

(72) Inventors: Sergey Puzhevich, Stutensee (DE);
Michael Kettenmann, Eppelheim (DE);
Christoph Jungkind, Walldorf (DE);
Matthias Weber, Heidelberg (DE)

(73) Assignee: SAP SE, Walldorf (DE)

( * ) Notice: Subject to any disclaimer, the term of this patent is extended or adjusted under 35 U.S.C. 154(b) by 128 days.

(21) Appl. No.: 15/498,367

(22) Filed: Apr. 26, 2017

(65) Prior Publication Data

US 2018/0311561 A1 Nov. 1, 2018

(51) Int. Cl.
| | | |
|---|---|---|
| *A63B 24/00* | (2006.01) | |
| *G06K 9/00* | (2006.01) | |
| *G16H 20/30* | (2018.01) | |
| *G09B 19/00* | (2006.01) | |

(52) U.S. Cl.
CPC ..... *G06K 9/00342* (2013.01); *G09B 19/0038* (2013.01); *G16H 20/30* (2018.01); *A63B 24/0021* (2013.01); *A63B 24/0062* (2013.01); *A63B 2024/0025* (2013.01); *A63B 2024/0028* (2013.01); *A63B 2024/0053* (2013.01); *A63B 2220/12* (2013.01); *A63B 2220/833* (2013.01); *A63B 2220/836* (2013.01); *A63B 2243/0025* (2013.01)

(58) Field of Classification Search
CPC .............. A63F 13/46; A63F 13/798; A63F 2011/0072; A63F 7/32; G06F 17/18; G06F 17/2818
See application file for complete search history.

(56) References Cited

U.S. PATENT DOCUMENTS

| | | | | |
|---|---|---|---|---|
| 5,513,854 | A * | 5/1996 | Daver | A63B 24/0003 |
| | | | | 348/157 |
| 6,441,846 | B1 * | 8/2002 | Carlbom | A63B 24/0021 |
| | | | | 348/157 |
| 9,882,592 | B2 * | 1/2018 | O'Hagan | G06K 7/10227 |
| 10,025,987 | B2 * | 7/2018 | Ackland | G06K 9/00724 |
| 2003/0054905 | A1 * | 3/2003 | King, Jr. | A63B 24/0021 |
| | | | | 473/467 |
| 2005/0032581 | A1 * | 2/2005 | Wagner | A63B 69/00 |
| | | | | 473/173 |

(Continued)

*Primary Examiner* — Jason T Yen
(74) *Attorney, Agent, or Firm* — Mintz Levin Cohn Ferris Glovsky and Popeo, P.C.

(57) ABSTRACT

A system for sensor-based tracking of participants of a sporting activity is provided. In some implementations, the system performs operations comprising determining, based on sensor data (e.g., information indicative of at least a location of a plurality of tracked participants and a location of a tracked object), a first probability of a team successfully scoring. The operations further comprise determining, in response to detecting an action which at least changes the location of the tracked object, a second probability of the team (or an opposing team (successfully scoring, and assigning, based on a difference between the first probability and the second probability, at least a portion of the difference among one or more of the plurality of participants. Related systems, methods, and articles of manufacture are also described.

18 Claims, 12 Drawing Sheets

(56) References Cited

U.S. PATENT DOCUMENTS

| | | | |
|---|---|---|---|
| 2007/0135243 A1* | 6/2007 | LaRue | A63B 24/0021 |
| | | | 473/467 |
| 2009/0111616 A1* | 4/2009 | Creelman | A63B 24/0021 |
| | | | 473/415 |
| 2010/0134614 A1* | 6/2010 | Aman | A63B 71/06 |
| | | | 348/135 |
| 2010/0184563 A1* | 7/2010 | Molyneux | A63B 24/0062 |
| | | | 482/1 |
| 2010/0283630 A1* | 11/2010 | Alonso | H04Q 9/00 |
| | | | 340/870.11 |
| 2011/0130643 A1* | 6/2011 | Derchak | A61B 5/0002 |
| | | | 600/409 |
| 2013/0066448 A1* | 3/2013 | Alonso | H04Q 9/00 |
| | | | 700/91 |
| 2015/0097700 A1* | 4/2015 | Holthouse | H04Q 9/00 |
| | | | 340/870.03 |
| 2015/0131845 A1* | 5/2015 | Forouhar | G06K 9/00724 |
| | | | 382/100 |
| 2015/0142142 A1* | 5/2015 | Campana Aguilera | |
| | | | A63B 71/06 |
| | | | 700/91 |
| 2016/0158625 A1* | 6/2016 | DeAngelis | A63B 71/0619 |
| | | | 340/539.13 |
| 2016/0361595 A1* | 12/2016 | O'Hagan | G06K 7/10227 |
| 2017/0032191 A1* | 2/2017 | Ackland | G06K 9/00724 |
| 2017/0165570 A1* | 6/2017 | Lucey | A63F 13/216 |
| 2018/0133579 A1* | 5/2018 | Huke | A63B 71/0616 |
| 2018/0176502 A1* | 6/2018 | Bhuruth | G06T 7/70 |

* cited by examiner

| ID | Account | A₁-O | A₁-D | A₂-O | A₂-D | A₃-O | A₃-D | ... | B₁-O | B₁-D | B₂-O | B₂-D | B₃-O | B₃-D | ... |
|---|---|---|---|---|---|---|---|---|---|---|---|---|---|---|---|
| Action₀ (game_start, A₁) | +0.10 | 0 | 0 | 0 | 0 | 0 | 0 | ... | 0 | -0.01 | 0 | -0.01 | 0 | -0.01 | ... |
| Action₁ (pass, A₁ A₂) | +0.10 | - | +0.10 | - | - | - | - | ... | - | -0.02 | - | -0.02 | - | -0.02 | ... |
| Action₂ (pass, A₂ A₃) | - | - | +0.20 | - | +0.20 | - | - | ... | - | -0.04 | - | -0.04 | - | -0.04 | ... |
| Action₃ (steal, A₃ B₁) | - | - | - | - | - | -0.70 | -0.2 | ... | - | - | +0.20 | +0.70 | - | - | ... |
| Action₄ (pass, B₁ B₂) | - | -0.38 | - | -0.38 | - | - | -0.38 | ... | +1.90 | - | +1.90 | - | - | - | ... |
| Action₄ (score, B₂ B₁) | - | -9.60 | - | -9.60 | - | - | -9.60 | ... | +64.0 | - | +32.0 | - | - | - | ... |
| ... | ... | ... | ... | ... | ... | ... | ... | ... | ... | ... | ... | ... | ... | ... | ... |
| Actionₙ (pass, B₁ B₂) | - | -0.01 | - | -0.01 | +0.01 | -0.01 | - | ... | +0.05 | - | +0.05 | - | - | - | ... |
| Actionₙ₊₁ (game_end, B₂) | +0.01 | - | +0.01 | - | +0.01 | - | - | ... | -0.01 | - | -0.01 | - | -0.01 | - | ... |

1110
Receive, for each of a plurality of tracked participants of a sporting-activity, data indicative of at least a location of each of the plurality of tracked participants

1120
Calculate, based on the data, a first probability that one or more of the plurality of tracked participants will successfully complete a sporting outcome

1130
Determine, based on the data, that an action occurred between at least two of the tracked participants

1140
Calculate, based on the data and in response to determining that the action occurred, a second probability that one or more of the plurality of tracked participants will successfully complete the sporting outcome

1150
Assign, based on a difference between the first probability and the second probability, at least a portion of the difference to the at least two of the tracked participants

1210 — Receive, for one or more of a plurality of tracked participants, first data indicative of at least a location of the one or more of the plurality of tracked participants

1220 — Receive second data indicative of at least a location of a tracked object

1230 — Determine, based on the first data and the second data, a first participant in possession of the tracked object

1240 — Calculate, based on the second data and historical data, a first probability that a first team successfully completes a scoring action

1250 — Determine, based on the first data and the second data, that a first action occurred between the first participant and a second participant

1260 — Calculate, based on the second data and in response to the first action, a second probability that a second team successfully completes the scoring action

1270 — Assign, based on a difference between the first probability and the second probability, at least a first portion of the difference to the first participant and/or the second participant

FIG. 12

SENSOR-BASED TRACKING OF SPORTS PARTICIPANTS

TECHNICAL FIELD

The subject matter described herein relates to sensor-based technologies, and more particularly, sensor-based tracking of participants of a sporting activity (e.g., athletes playing a game).

BACKGROUND

In the world of sports (e.g., professional or collegiate sports), infinite possibilities exist for evaluating the relative skill of participants of a sporting activity (e.g., athletes). However, most of these evaluations rely on the same basic data, such as scoring events or other discrete, measureable events (e.g., rebounds, steals, passes completed, and/or the like) in addition to the gut feel of the person doing the evaluating (e.g., sports agents or scouts). Furthermore, many statistical evaluations of participants are not possible to observe or track with human senses (e.g., strength and speed), and other evaluations simply involve too many variables for humans to monitor in a practical manner. Accordingly, it can be desirable to leverage sensor-based tracking technologies to monitor and/or evaluate participants of a sporting activity.

SUMMARY

In some aspects, a method, computer program product and system are provided. In an implementation, a sensor-based tracking system is provided. The system can include (or otherwise utilize) at least one processor and/or memory, which can be configured to perform operations including determining, based on first data (e.g., information indicative of at least a location of one or more of a plurality of tracked participants of a sporting event) and second data (e.g., information indicative of at least a location of a tracked object), a first probability of a first team successfully completing a sporting outcome, wherein the plurality of tracked participants includes the first participant and a second participant. The operations further comprise determining, in response to detecting an action (between the first participant of the first team and the second participant of a second team) which at least changes the location of the tracked object and based on a new location of the tracked object, a second probability of the second team (which may be the same or different from the first team) successfully completing the sporting outcome. The operations further include assigning, based on a difference between the first probability and the second probability, at least a portion of the difference to the first participant and/or the second participant.

In some variations, the operations further comprise receiving, at a server, the first data and the second data from a plurality of sensors deployed within an area of interest, and/or the plurality of sensors comprise at least one of an accelerometer, a gyroscope, a geo-spatial sensor, and a global positioning sensor.

In some implementations, the operations further comprise identifying, based on the first data and the second data, that the first participant is in possession of the tracked object, and/or identifying, based on the first data and the second data, that the second participant has taken possession of the tracked object, wherein the action comprises the second participant taking possession of the tracked object. In some aspects, the first participant is not on a same team as the second participant, and assigning at least a portion of the difference comprises assigning a negative value to an offensive account of the first participant, wherein the negative value comprises at least a portion of a negative of the first probability.

In some variations, the operations further comprise identifying, based on the first data and the second data, that a third participant is at least partially at fault for the action occurring, wherein the first participant is on a same team as the second participant, wherein the third participant is not on the same team as the second participant, and wherein assigning at least a portion of the difference comprises (a) assigning a positive value to an offensive account of the first participant, wherein the positive value comprises at least a portion of the difference; and/or (b) assigning a negative value to a defensive account of the third participant, wherein the negative value comprises at least a portion of a negative of the difference.

In some variations, the operations further comprise determining, based on the first data and the second data, that the second participant successfully completed the sporting outcome, wherein the sporting outcome comprises a goal scored on an opposing team. In related aspects, the operations further comprise assigning, based on a second difference between the second probability and a value of one, at least a portion of the second difference to an offensive account of the second participant. In similar implementations, the operations further comprise assigning, in response to the action comprising a pass from the first participant to the second participant, at least a portion of the second difference to an offensive account of the first participant.

Implementations of the current subject matter can include systems and methods consistent with the present description, including one or more features as described, as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 4 depicts a data structure for tracking sensor-based actions, in accordance with some example implementations;

FIG. 11 depicts an example of a method for tracking and/or analyzing participants in a sporting event, in accordance with some example implementations; and FIG. 12 depicts another example of a method for tracking and/or analyzing participants in a sporting event, in accordance with some example implementations.

When practical, similar reference numbers denote similar structures, features, or elements.

DETAILED DESCRIPTION

As noted above, it can be desirable to leverage sensor-based tracking technologies to monitor and/or evaluate participants of a sporting activity. Doing so can provide additional insight to the value and/or skill level of players which would not otherwise stand out in terms of traditional statistical methodologies. For example, most sports professionals (e.g., players, analysts, scouts) will appreciate that assists are a very valuable statistic in determining a player's value relative to other players. However, some participants of a sporting activity may consistently place their teammates in a position to score, but won't get credit for assists when their teammates repeatedly miss opportunities to score. Numerous other player actions or outcomes (e.g., defensive actions, movement away from the ball or otherwise not closely correlated with an actual scoring event) may not be readily captured by current approaches to quantifying player value. Accordingly, systems and methods for sensor-based tracking of participants during sporting events/activities are described.

As used herein, the term sensor can encompass physical sensors and/or virtual sensors. Virtual sensors can include techniques such as filtering, which may be used to "sense" (e.g., identify) one or more objects (e.g., participants of a sporting activity) in a video, through a lens, and/or the like.

Figure 1:
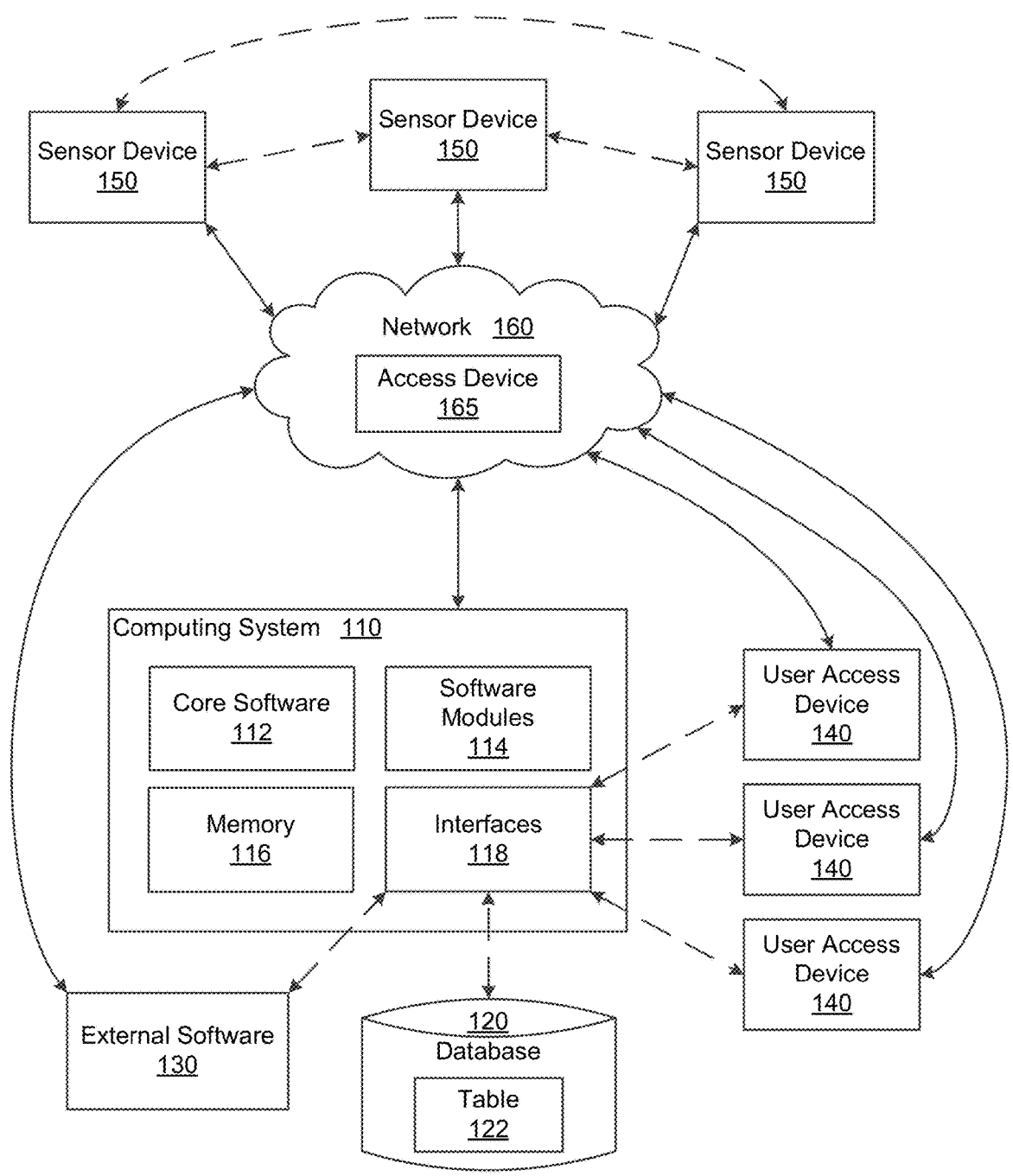
FIG. 1 depicts a block diagram of a system for sensor-based tracking, in accordance with some example implementations.

FIG. 1 illustrates a functional block diagram of a system 100 in which features consistent with the described subject matter may be implemented. As illustrated, the system 100 can include a computing system 110 capable of communicating with a database 120, external software 130, one or more user access devices 140, and/or one or more sensor devices 150. In some aspects, the computing system can utilize one or more interfaces 118 for communication. Communication among the devices in the system 100 can be through the use of direct communications, such as through the use of a wireless connection like Bluetooth, near-field communication (NFC), ZigBee, WiFi, some combination thereof, and/or the like. Additionally or alternatively, communication among the devices in the system 100 can be through the use of a hard wire connection such as universal serial bus (USB) and/or the like. Communication can additionally or alternatively occur through indirect communications, such as over a network 160, which can include a local area network, a wide area network, a wireless network, the Internet, some combination thereof, and/or the like.

Communication over the network 160 can utilize a network access device 165, such as a base station, a Node B, an evolved Node B (eNB), an access node (AN), a hotspot, and/or the like. In some aspects, any of the user access device 140 and/or the sensor devices 150 can include personal computers, desktop computers, laptops, workstations, cell phones, digital media devices, smart phones, smart watches, PDAs (personal digital assistants), tablets, hardware/software servers, sensors, terminals, access terminals (ATs), mobile stations, user equipment (UE), subscriber units, and/or the like. In some implementations, one or more of the sensor devices 150 can include any number (including zero) or combination of accelerometers, gyroscopes, magnetic sensors, pressure sensors, infrared sensors, geo-spatial sensors, global positioning sensors (GPS), cameras, and/or the like, which can be utilized to characterize position, motion, speed, acceleration, and/or the like of an object or person to which the sensor is affixed or at which the sensors are directed. Wired or wireless communication among the computing system 110, user access devices 140, and/or sensor devices 150 can occur according to various protocols and/or access technologies (e.g., Global System for Mobile Communication (GSM), Universal Mobile Telecommunications System (UMTS), technologies developed by IEEE such as WiFi and/or Bluetooth, technologies developed by the Third Generation Partnership Project (3GPP) or 3GPP2 such as Long Term Evolution (LTE) and/or CDMA2000, etc.).

In some aspects, one or more of the sensor devices 150 can be configured to operate and/or communicate according to low-power techniques. For example, the sensor devices 150 can be configured to utilize less battery power, less processing power, sleep states, and/or the like. In some implementations, at least a portion of the sensor devices 150 can be autonomous or semi-autonomous. For example, the sensor devices 150 can store configuration information for themselves and/or for other sensor devices 150. Thus, a user may be able to access one sensor device 150 and change the configuration of other sensor devices 150, such as any other sensor device 150 that is, for example, in a chain with the accessed sensor device 150. Software modifications/updates may be provided to multiple sensor devices 150 in a similar manner. In some implementations, a "chain" can be established among sensor devices 150 via blockchain techniques to exchange data and/or provide guarantees about the data. In some implementations, blockchain techniques can include the use of a distributed database that maintains a continuous/growing list of records (e.g. "blocks"), which can be secured from tampering/revision, and/or contain timestamps and/or links to a previous block. Information may be additionally or alternatively provided/maintained in other ways and/or according to other techniques. In some aspects, one or more of the sensor devices 150 can include and/or be regarded as Internet of things (IoT) devices.

As illustrated, the computing system 110 can include core software 112 and/or one or more software modules 114. The core software 112 can provide one or more features of a high-level programming software system. The software modules 114 can provide more specialized functionality. For example, the core software 112 and/or software modules 114 can include sensor management, database management, and/or data anonymization features. In some aspects, the core software 112 or other similar software/hardware can be capable of accessing a database layer, such as the database 120 including at least one table 122 having at least one column/row. The database table 122 can store any kind of data, potentially including but not limited to operational data retrieved from sensor devices 150, historical data, and/or the like. In some implementations, the database table 122 can include master data, metadata, definitions of scenarios, definitions of processes, configuration information, and/or the like.

In some aspects, the core software 112 can be configured to load the information from the database 120 to memory 116 (e.g., main memory) in response to receipt of a query instantiated by a user or computer system through one or more sensor devices 150, user access devices 140, the external software 130, and/or the like. In some implementations, all, substantially all, or at least a large amount of the operational data of the database 120 can reside in-memory (e.g., in random-access memory (RAM)). Although the database 120 is illustrated as being separate and, at times, described as being separate from the computing system 110, in various implementations, at least a portion of the database 120 can be located within the computing system. The database 120 may be a column store database and/or the computing system 110 may be configured to perform OLTP (online transaction processing) and/or OLAP (online analytical processing), which can include complex analytics and tasks.

In some aspects, one or more of the software modules 114 can be configured to utilize data stored in the memory 116, data stored in the database 120, and/or data otherwise accessible to the computing system 110. As further illustrated, the computing system 110 can be capable of utilizing external software 130. In some aspects, the external software 130 can provide additional functionalities or services which may not be available at the computing system 110. In some aspects, the external software 130 may include cloud services. In some aspects, the computing system 110 can aggregate or otherwise provide a gateway via which users can access functionality provided the external software 130. In some implementations, the database 120 and/or the external software 130 can be located across one or more servers, and/or communication among the computing system 110, the database, and/or the external software 130 can occur over the network 160.

At least a portion of the illustrated system 100 may include hardware and/or software that interacts with a database, users, and/or other software applications for defining, creating, and/or updating data, for receiving, handling, optimizing, and/or executing database queries, and/or for running software/applications (e.g., software modules 114, and/or external software 130) which utilize a database. In some aspects, the database 120 can be a structured, organized collection of data, such as schemas, tables, queries, reports, views, and/or the like, which may be processed for information. The database 120 may be physically stored in a hardware server or across a plurality of hardware servers. In some aspects, the system 100 may be implemented as a cloud-based system and/or an IoT system.

Figure 2:
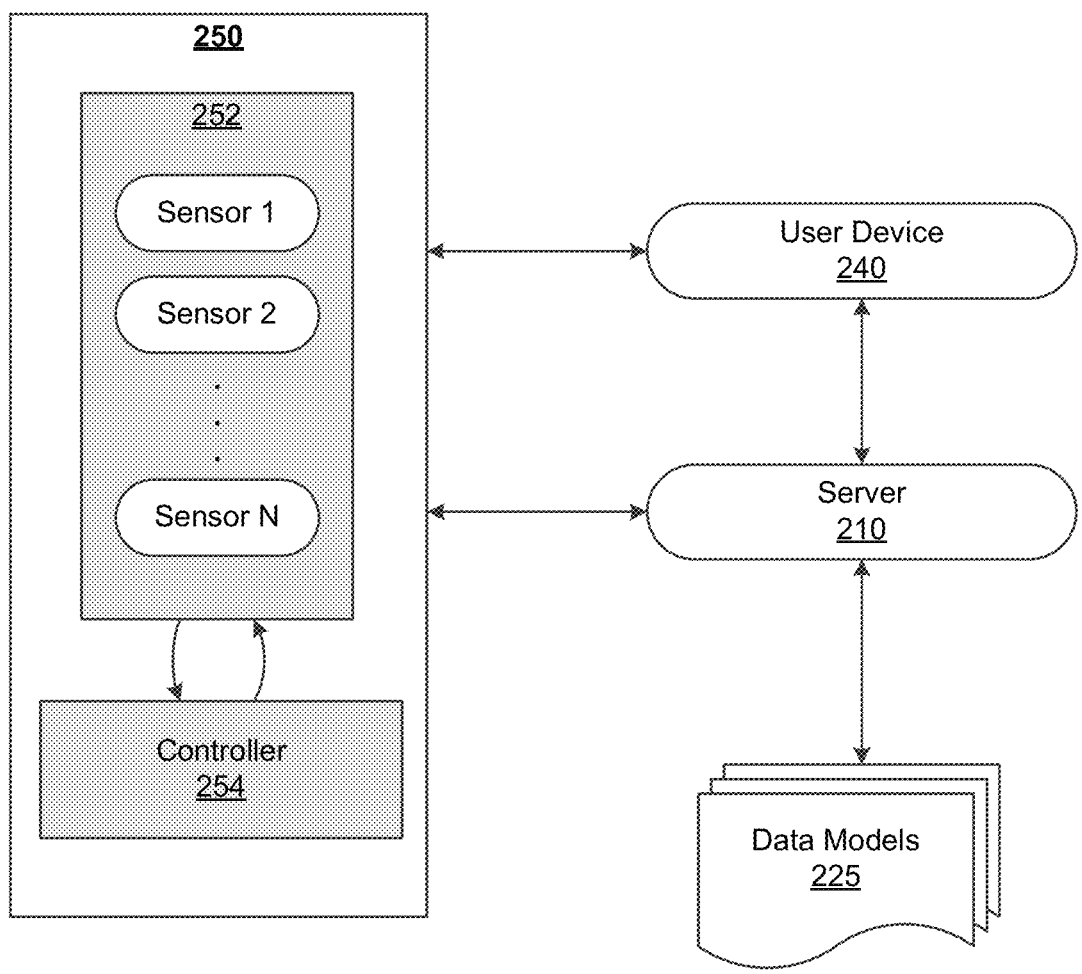
FIG. 2 depicts a block diagram of a system for processing and/or obtaining data from a plurality of sensors, in accordance with some example implementations.

Although not illustrated, in some aspects, a centralized device may control one or more of the sensor devices 150 and/or one or more of the user access devices 140 may be in communication with one or more of the sensor devices 150. For example, FIG. 2 depicts a block diagram of a system 200 for processing and/or obtaining data from a plurality of sensors, in accordance with some example implementations. In some aspects, the system 200 can form at least a portion of the system 100 of FIG. 1.

As illustrated, a sensor system 250 can include a plurality of sensors 252 (shown as sensors 1-N) and/or a controller 254. The sensor system 250 and/or each of the plurality of sensors 252 can be similar to a sensor device 150 of FIG. 1. In some aspects, there can be multiple sensor systems 250 deployed within an area of interest, and each sensor system 250 can utilize its own respective controller 254 to process information from and/or provide information to a respective set of sensors 252. In other aspects, there can be a singular sensor system 250 which utilizes a centralized controller 254 to process information from and/or provide information to a set of sensors 252 deployed within an area of interest.

The sensor system 250, through one or more communication interfaces, can communicate with a user device 240 and/or a server 210. Similarly, the user device 240 can be in communication with the server 210. The server 210 and/or the user device 240 can process information received from the sensor system 250 to process data obtained from any number of the plurality of sensors 252 to determine information, such as location, speed, velocity, direction of motion, and/or other information of a respectively tracked person or object. In some aspects, the processing of the information from the sensor system 250 can be based on data models 225, which can dictate what sensor data means and/or how sensor data should be processed. For example, in some implementations, data models 225 can dictate a format for processing and/or storing sensor data.

Figure 3:
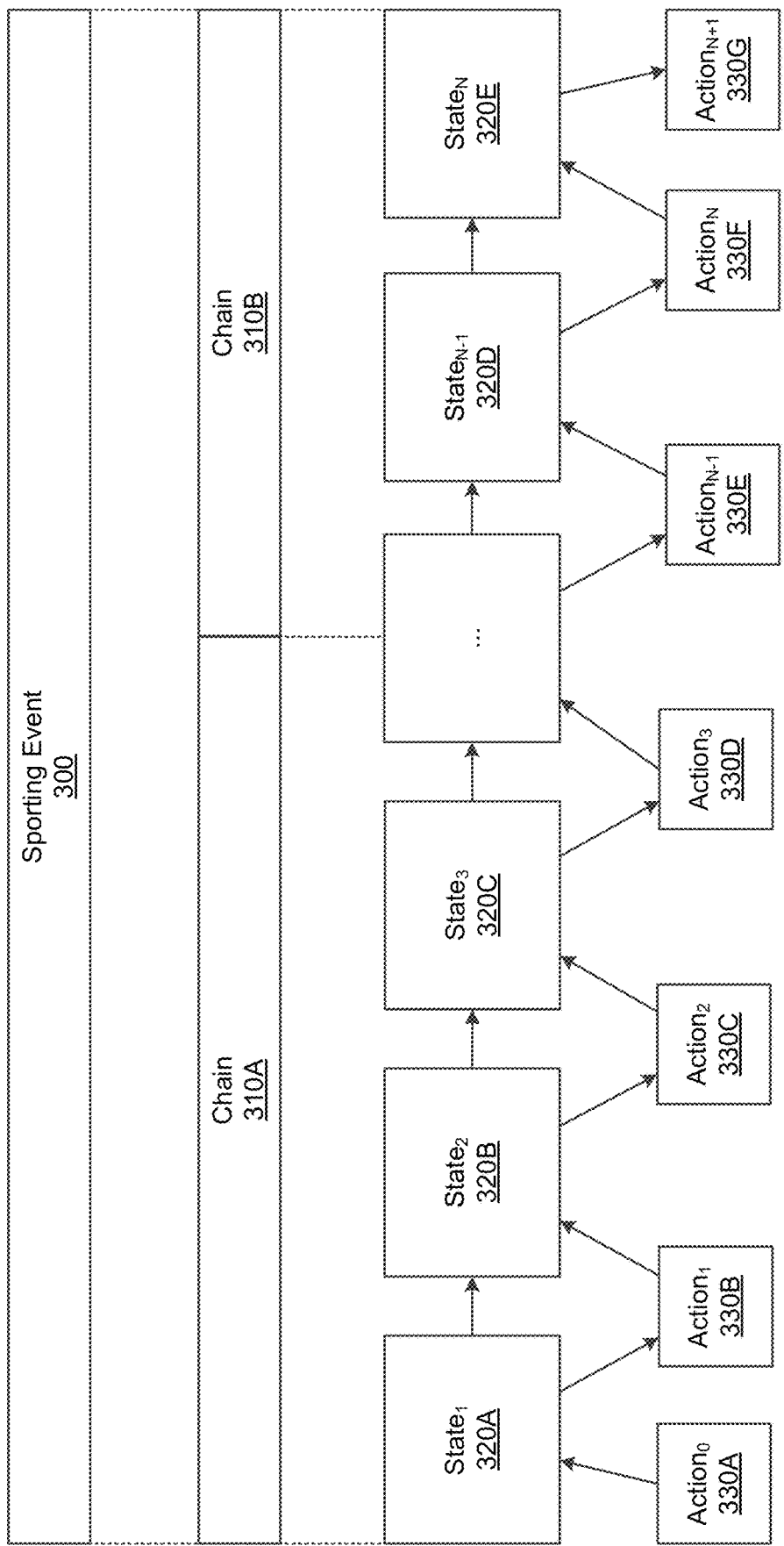
FIG. 3 depicts data structures for sensor-based tracking, in accordance with some example implementations.

FIG. 3 depicts data structures which can be used for sensor-based tracking, in accordance with some example implementations. As illustrated, a series of consecutive states 320A-E (also referred to herein collectively as "states 320" or individually as a "state 320") can be used to track what has occurred/is occurring within the confines of a sporting event 300. In some aspects, each state 320 can include information that is indicative of what is occurring within an area of interest (e.g., a field) for the sporting event 300.

For example, one or more of the states 320 can include attributes, such as one or more of player information, information regarding a tracked object (e.g., a ball or puck), a current score, timing information, weather information, a unique identifier of the state 320, and/or the like.

In some implementations, a mathematical expectation (e.g., a numerical probability value ranging from zero and one) can be calculated and/or assigned, based on one or more of the attributes, such as a location of the tracked object. In some implementations, the mathematical expectation can be an expectation of the result (e.g., a score) that can be achieved from the current state 320. This expectation can depend on what a result of a sporting event 300 is defined as and/or a goal set for the sporting event 300. For example, in championship games, the expectation can be the number of points awarded for the sporting event 300, depending on its outcome. In this case, every state 320 can be evaluated as a mathematical expectation of points, which can be evaluated based on attributes of the state. In a play-off game the result can be qualifying (e.g., "1") or not qualifying (e.g., "0") and evaluation of each state can be a probability of qualifying based on the state 320. In simpler implementations, the result can be based on the number of goals scored and/or the number of goals conceded. In some aspects, the state 320 value can include a probability of scoring and/or conceding a goal, based on information relating to the current situation of the sporting event 300. This probability can be estimated in different ways, including statistically, through applying machine learning algorithms, and/or performed by a human heuristically.

For example, as the object gets closer to an opponent's goal, the probability of a sporting outcome (e.g., a goal) occurring can increase. Although the scoring probability can be based on distance away from a goal, additional/alternative information can be utilized to calculate the scoring probability, such as historical data. For example, in some implementations, location information of an object, for each of a plurality of scores over some period of history within a given sport (e.g., professional club soccer, national league soccer, other levels of play, and/or other sports), can be recorded and/or analyzed to determine a historical probability of a score occurring based on the current location of the object (e.g., ball or other object involved in playing the relevant sport).

In some implementations, the score probability can be based on additional information, such as the locations of one or more of the players, the current score, the current weather, how much time is left in the sporting event 300, and/or the like. For example, if a relatively good defender is close enough to (e.g., a threshold distance away from and/or moving at a certain speed towards) the object, the probability of scoring can be calculated to be lower than an instance where the defender is not close to the object. In some aspects, the score probability of a given state 320 can be regarded as a value of the state 320.

With respect to player information, the state 320 can include information on each player in a field of interest, such as those within the field of play and/or those near the field of play (e.g., on a bench, in a penalty area, in a locker room, and/or the like). The information tracked for each player can include an identifier for the player (which can be based on identifier(s) of the sensor(s) attached to/worn by the player), a current location of the player, a position of the player, an indication of whether the player is on offense or defense, a current direction of motion for the player, a speed of the player, a velocity of the player, and/or the like. In some aspects, the current location of the player can be absolute and/or relative (e.g., their physical location within the pitch). In some implementations, the "position" of the player can include the position which the player is assigned in the game, such as striker, forward, midfielder, defender, goalie, point guard, center, guard, tackle, tight end, quarterback, running back, wide receiver, nose guard, linebacker, corner, safety, any variations thereof, and/or the like.

In some implementations, and area of interest can be marked through the use of various technologies, such as geo-fencing technologies. Based on a current position of any given player and sensors or other devices defining a geographical area for one or more areas of interest, it can be determined whether a player is playing in the current sporting event 300, sitting on the bench, in the locker room, in a penalty box, and/or the like.

With respect to the tracked object, each state 320 can include an identifier for the object, a current location of the object, a current direction of motion of the object, a current speed of the object, a velocity of the object, and/or the like. As noted above, historical information for the object (including any number of the above data points) can be maintained and/or utilized to determine statistical probabilities of a score occurring during any given state 320.

The scoring information for the state 320 can include a score for the home team and a score for the visiting team. The timing information for the state 320 can include a timestamp, the time elapsed, and/or the time remaining in the game and/or current period (e.g., half, quarter, etc.). The weather information can include weather information, which can be based in different levels of granularity (e.g., sunny or cloudy, precipitation/humidity levels, temperature, wind chill, and/or the like).

As further illustrated, chains 310A-B can be data structures used to track sensor-based information. In some implementations, each chain 310A-B can terminate at the occurrence of a particular sporting event, such as a goal and/or the end of a game/period for a sporting event 300. Accordingly, each chain 310A-B can start at the occurrence of a particular sporting event, such as a start of a game/period for a sporting event 300 and/or after a goal. Although the sporting event 300 is shown as the largest data structure, other data structures including multiple sporting events 300 can be used, such as a season, a year, a team history, and/or the like.

As shown, the beginning and/or the end of each state 320 can be dictated by the occurrence of an event 330A-G (also referred to herein collectively as "events 330" or individually as an "event 330"). Each event 330 can include information such as a type for the event, an indication of one or more players involved in the event, and/or the like. For example, a type for any given event 330 can include at least one of a pass, a shot, a foul, a steal (or some other change in possession), a game start, a period end, a period start, a game end, and/or the like. Any players identified as being participants for the event 330 can be identified based on an identifier or some other indicia.

In some implementations, credit and/or fault can be assigned to a given player based on a determination that the player was responsible for at least a portion of the event 330 occurring. For example, if one player successfully passes a ball to another player, then one or both of the players can be credited (at least in part) with the event 330 occurring. Similarly, if a player is close enough to the ball but is determined to have unsuccessfully stopped the event from occurring, the player can be faulted (at least in part) with the event 330 occurring.

FIG. 4 depicts a data structure 400 for tracking sensor-based actions, in accordance with some example implementations. In some aspects, the data structure 400 can be utilized to keep track of credit and/or fault of each player involved in a sporting event 300. Accordingly, the following description is described with respect to both FIG. 3 and FIG. 4. In some aspects, each player can have two "accounts," including an offensive account (illustrated as "O") and a defensive account (illustrated as "D"). Keeping two separate accounts helps to realize that players can have different roles which should be treated differently.

As illustrated, the first row in the data structure 400 can include an "initialization" action ($Action_0$), which can be a start of a sporting event 300. In order to create this action, it may be determined that player $A_1$ is closest to the ball, and is therefore taking the kickoff. However, other methods of determining who is the first person to take possession of the ball at the start of the sporting event 300 are possible. Additionally or alternatively, a probability of player $A_1$ scoring, based on the position of the ball (and/or other information), can be determined. This probability can then be assigned to a first state 320A. In some implementations, a difference between the probability for a new/subsequent state 320B and the previous state 320A can be calculated and/or assigned to the action 330B which caused the transition between the states 320A, 320B. The value assigned to the action 330B, in some implementations, can be distributed among one or more of the players (e.g., players within the field of play).

In some implementations, a probability of scoring at the start of the game can be assigned to the first state 320A and/or the difference between that probability and zero can be assigned to the initialization action 330A which triggered the creation of the first state 320A. For example, as illustrated, if the probability of scoring at the start of the sporting event 300 is 0.1%, then the offensive account of player $A_1$ can be credited with the 0.1% chance of scoring, as player $A_1$ took possession of the ball and earned this opportunity for his team. However, in some implementations, the first state 320A and/or the initialization action 330A can be assigned a value of zero. Accordingly, the first player $A_1$ to take possession of the ball at the beginning of a sporting event 300 (or some portion thereof, such as at the start of a new period and/or for a kickoff after an opponent scores) may not be credited with anything until they perform the first action 330B after the initialization action 330A. Although 0.1% is illustrated in the data structure 400 as a value 0.1 (instead of 0.001), this is for the purpose of simplification and readability, as some implementations can involve storing values equal to each of the illustrated values divided by one hundred.

On the defensive side, one or more of the players $B_{1-X}$ (where X represents the number of players in the field of play and/or on the team) can be debited with at least a portion of the increased chance of scoring that was gained by the opponent (e.g., through player $A_1$). For example, assuming that no player was at fault for player $A_1$ obtaining possession of the ball at the start of the sporting event 300, then each player can be debited with the increase afforded to the opposing team, divided by the number of players on the field. For the purposes of simplification, it is assumed that each team has exactly ten players in the field of play at any given time. Accordingly, in the initialization step, each of the ten players on team B are debited by 0.01% (0.1%/10) on their defensive account.

In some implementations, a goalie might not be penalized for actions where no player is at fault. This could mean that if each team has ten players on the field outside of their respective goalies, then the debited amount could be divided by ten and distributed to all players other than the goalie. Although these approaches can appear to over-penalize the opposing team, the actual "penalty" is very small, and doing so can help to keep a balance of all offensive and defensive actions. For example, in some implementations, the total of all of the offensive accounts/actions of a first team, minus the total of the defensive accounts/actions of a second team (opponent), can equal the score of the first team. Similarly, in some implementations, the total of all of the offensive accounts/actions of the second team, minus the total of the defensive accounts/actions of the first team, can equal the goals scored against (conceded by) the first team.

Figure 5:
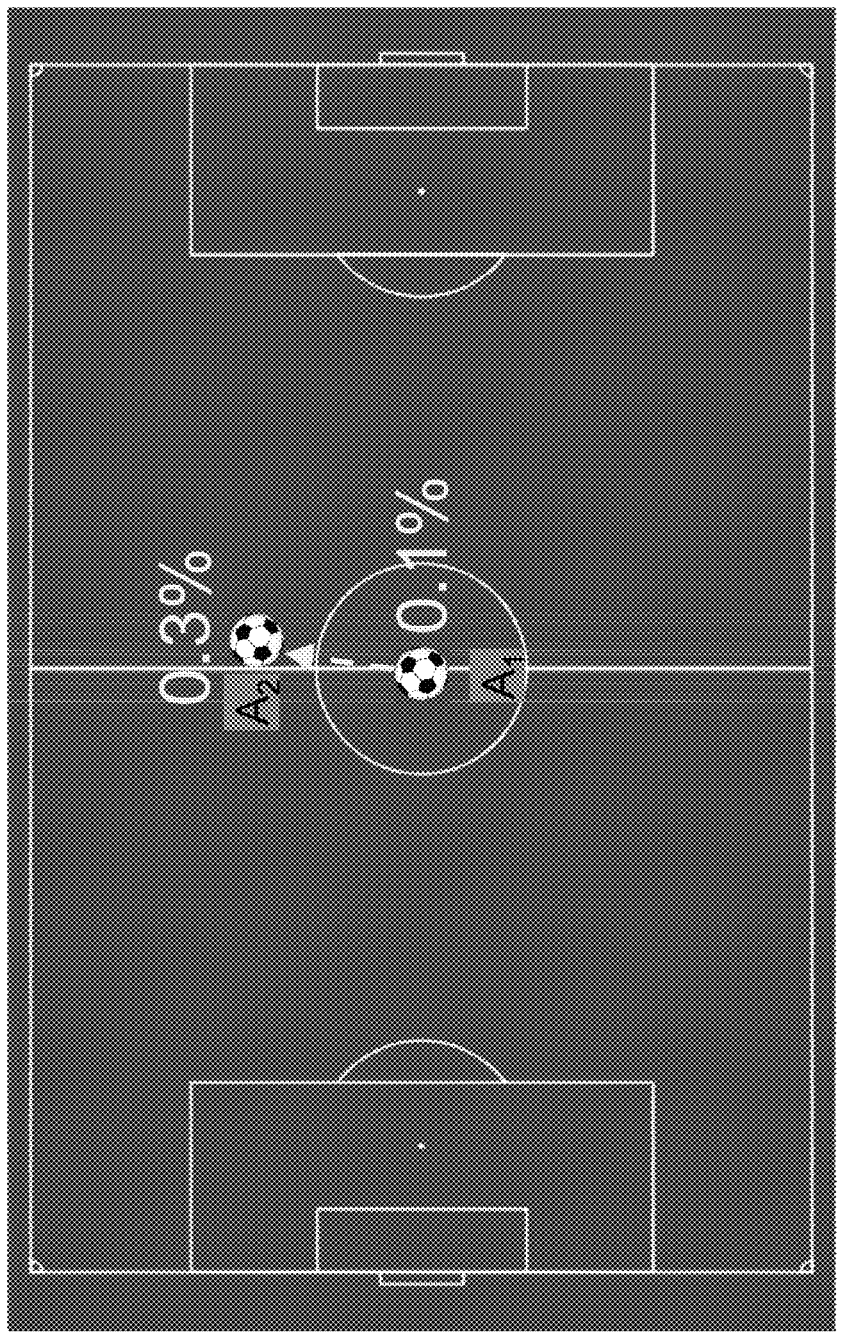
FIG. 5 depicts an example illustration of relative probability outcomes associated with a first sensor-based action, in accordance with some example implementations.

As illustrated in the second row of the data structure 400, after the initialization action, a first action can occur, which can be a pass from player $A_1$ to player $A_2$. The occurrence of this action can trigger the termination of the first state 230A and the beginning of the second state 320B. FIG. 5 depicts an example illustration of relative probability outcomes associated with the first sensor-based action 330B, in accordance with some example implementations. As illustrated, the probability of the current attack of team A ending successfully (e.g., scoring a goal) was initially 0.1%, but when player $A_1$ passes the ball to player $A_2$, the probability of the current attack of team A ending successfully can increase to 0.3%. This new probability (0.3%) can be determined and/or assigned as the value of state 320B. An attack may include several stages, passing from one player to another, and can be even interrupted by fouls, but may still counts as one attack as long as the sane team still possesses the ball. In some aspects, the probability used to evaluate any state 320 can include all possible variants of how situation(s) on the field may develop from this state 320, rather than just statistical evaluation of the state if a direct shot would be taken from the current position.

The value of state 320B can be compared against the previous probability of a score occurring, based on the value assigned to state 320A. Here, the difference can be 0.2%, which can be credited, at least in part, to one or more of player $A_1$ and player $A_2$. For example, in the illustrated data structure 400, each of player $A_1$ and player $A_2$ can be credited with half of the value of the increased chance of scoring (e.g., +0.1% each). However, other methods of distribution are possible.

On the defensive side, each player of team B can be debited with a proportionate amount of this increase (e.g., 0.2%/10=0.02%). In some aspects, this proportionate debiting can be based on a determination that no specific player on team B was at fault for the increase in probability. In some aspects, if the pass from player $A_1$ to player $A_2$ decreased the probability of team A scoring, then each of the players on team B may be credited with a positive increase in each of their defensive accounts.

Figure 6:
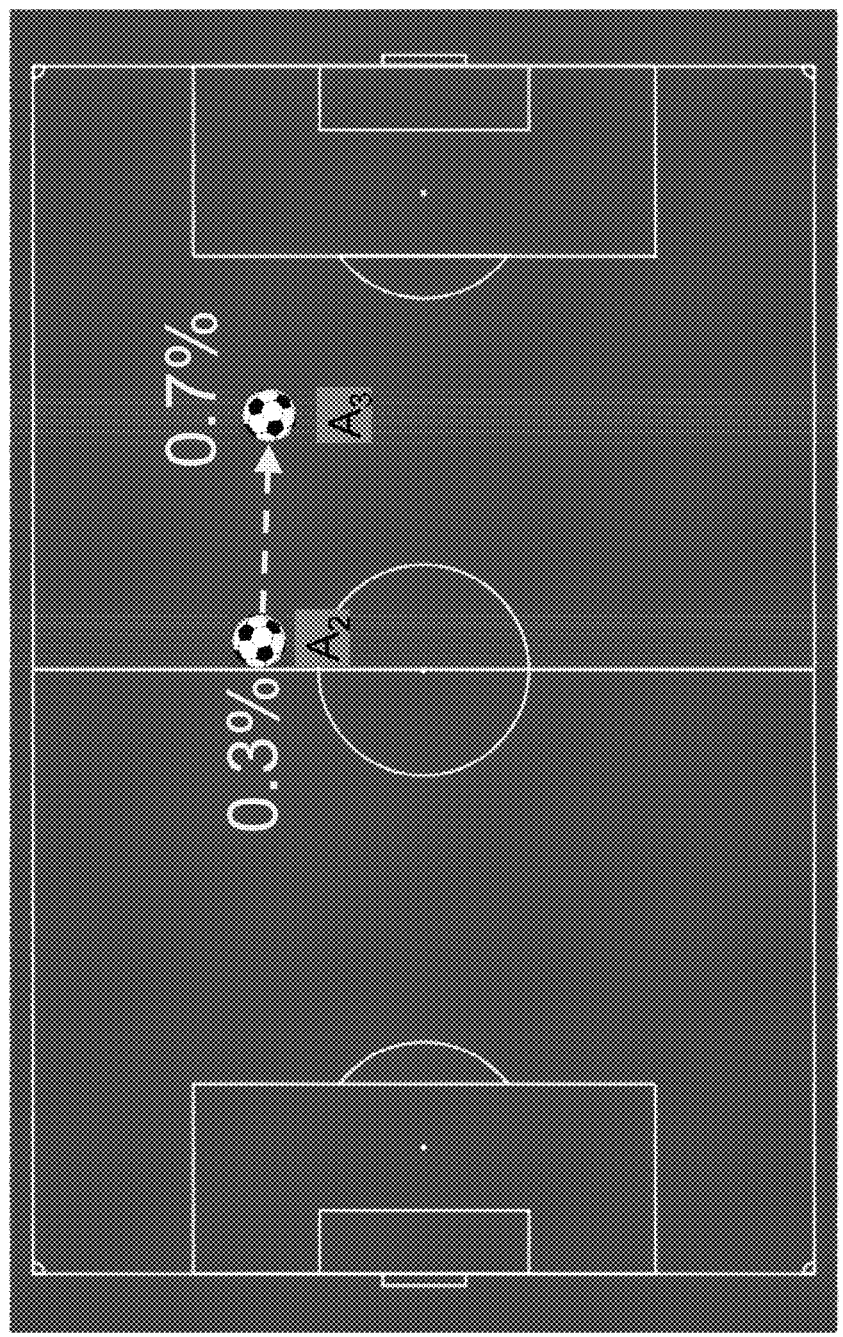
FIG. 6 depicts an example illustration of relative probability outcomes associated with a second sensor-based action, in accordance with some example implementations.

Subsequent to the first action, a second action 330C can occur, which can be a pass from player $A_2$ to player $A_3$. FIG. 6 depicts an example illustration of relative probability outcomes associated with the second sensor-based action 330C, in accordance with some example implementations. As illustrated, the pass can increase the chances of team A scoring (e.g., on the attack) from 0.3% (state 320B) to 0.7% (state 320C), which is an increase of 0.4%. Accordingly, in some implementations, player $A_2$ can be credited with a 0.2% increase in their offensive account, player $A_3$ can be credited with a 0.2% increase in their offensive account, and/or each of the players on team B can be debited with a 0.04% decrease in their defensive account.

If it was determined that player $B_1$, for example, was at fault for the successful completion of the action 330C, then player $B_1$ could be debited with the entire 0.4% decrease in their defensive account, and no other members of team B would be debited for action 330C. Similarly, if it was determined that player $B_1$ and player $B_2$, for example, were both (e.g., equally or otherwise) at fault for the successful completion of the action 330C, then player $B_1$ could be debited with a 0.2% decrease in their defensive account, player $B_2$ could be debited with a 0.2% decrease in their defensive account, and no other members of team B would be debited for action 330C.

Figure 7:
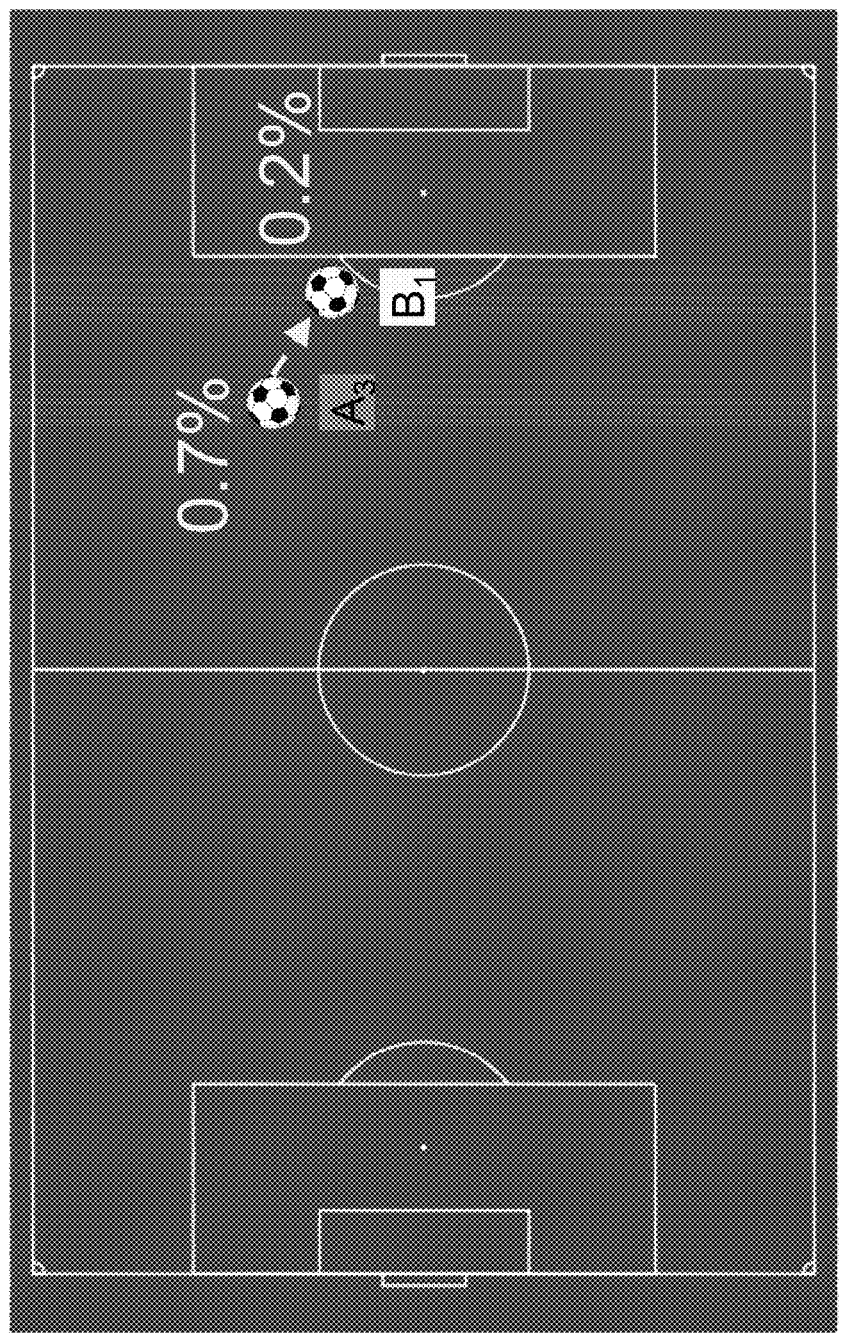
FIG. 7 depicts an example illustration of relative probability outcomes associated with a third sensor-based action, in accordance with some example implementations.

Subsequent to action 330C occurring, action 330D may occur, which can be player $B_1$ taking the ball from player $A_1$. FIG. 7 depicts an example illustration of relative probability outcomes associated with the third sensor-based action 330D, in accordance with some example implementations. As illustrated, player $A_3$ has lost a 0.7% chance of scoring for their team, and player $B_1$ had gained a 0.2% chance of scoring for their team. Accordingly, player $A_3$ can be debited with the entire 0.7% chance lost in their offensive account, player $B_1$ can be credited with the stop/steal by an increase of 0.7% in their defensive account, player $A_1$ can be debited with a 0.2% decrease in their defensive account, and/or player $B_1$ can be credited with a 0.2% increase in their offensive account.

Figure 8:
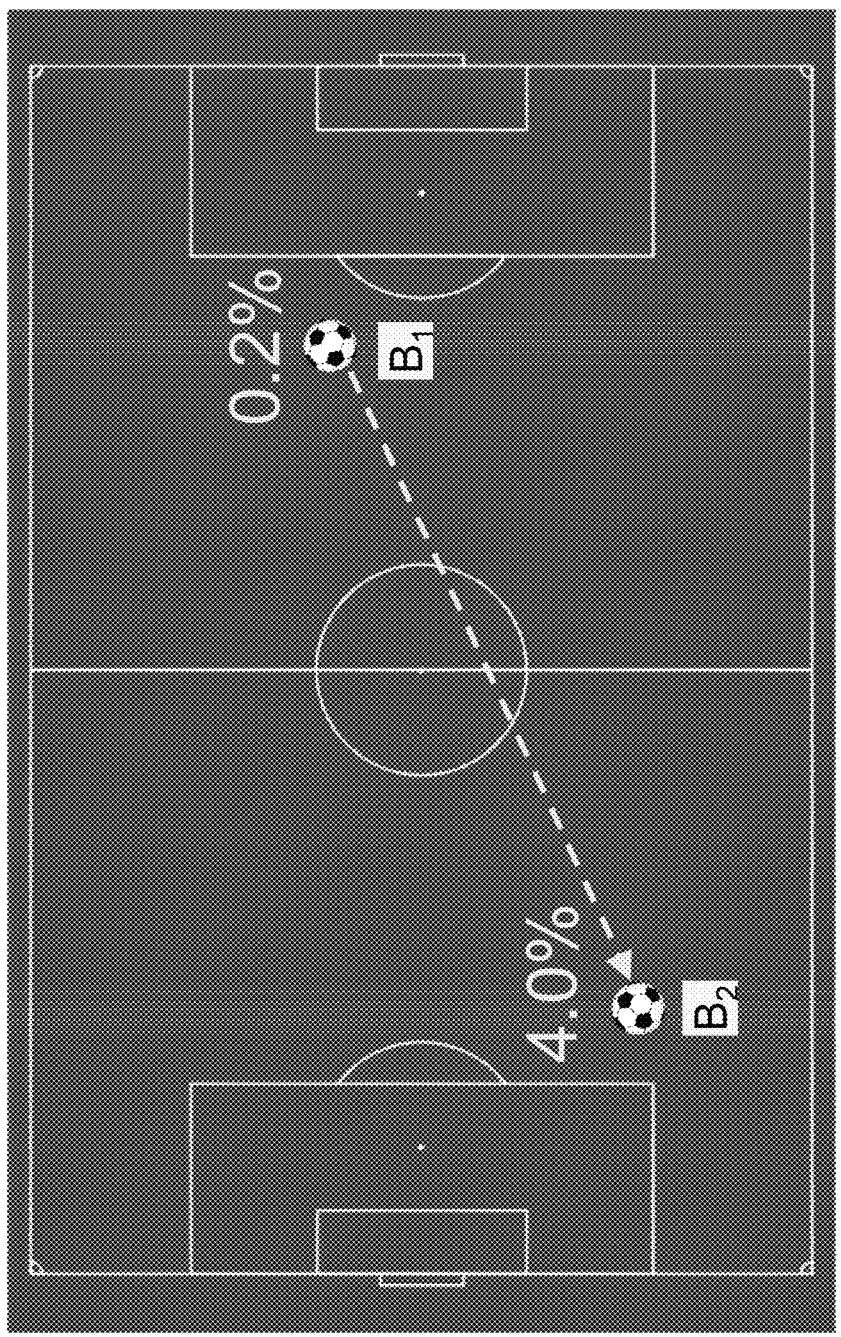
FIG. 8 depicts an example illustration of relative probability outcomes associated with a fourth sensor-based action, in accordance with some example implementations.

After the steal, player $B_1$ can pass the ball to player $B_2$, which can increase the probability of team B scoring by 3.8%. FIG. 8 depicts an example illustration of relative probability outcomes associated with this fourth sensor-based action, in accordance with some example implementations. Based on this increase, players B1 and B2 can receive a 1.9% credit in their offensive accounts, and each of the members of team A can receive a 0.38% debit in their defensive accounts (e.g., if no specific player(s) are assigned with fault of this action).

If the pass from player $B_1$ to player $B_2$ results in a foul (e.g., offside), then the action 330 can be considered a foul (e.g., assigned an attribute/type of "foul" or some indication thereof), player $B_1$ and/or player $B_2$ can be debited with at least a portion of the lost offensive opportunity (e.g., 0.2%) to their offensive account. Additionally or alternatively, player $B_1$ and/or player $B_2$ can be debited with at least a portion of a probability of the opponent scoring, as determined for/assigned to the next state 320 (e.g., based on the spot of the ball after the foul), to their defensive account. In some implementations, a foul by a player of team A against a player of team B, for example, can penalize the player from team A causing the foul, which results in a state 320 that has a higher probability of team B scoring (e.g., a penalty that results in a free kick). In the event that a player clears the ball and it is intercepted by a defending player, then the player clearing the ball may still net a positive credit to their offensive and/or defensive accounts if, for example, the location of the interception provides the opposing team with a lower probability of scoring than the probability of the team clearing the ball scoring at the time the ball was cleared).

Figure 9:
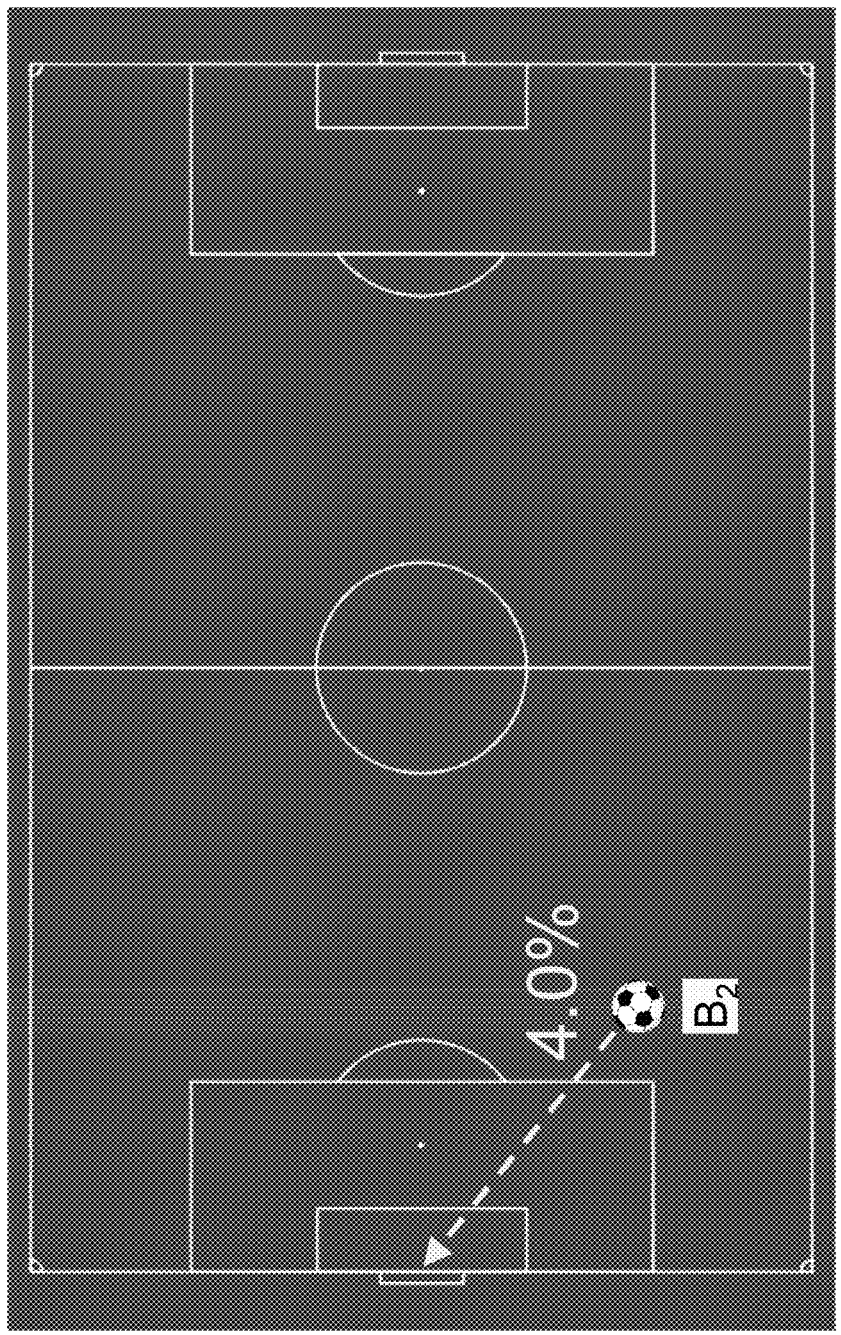
FIG. 9 depicts an example illustration of relative probability outcomes associated with a fifth sensor-based action, in accordance with some example implementations.

Subsequent to player $B_2$ receiving the pass, player $B_2$ may shoot and score. FIG. 9 depicts an example illustration of relative probability outcomes associated with a fifth sensor-based action, in accordance with some example implementations. As a result, the difference between the one and the probability of scoring can be attributed to the offensive account of player $B_2$. However, in some implementations, some credit can be given to the offensive account of one or more players which assisted player $B_2$ in the goal. The proportions used for each assisting player, whether a pass counts as an assist, and/or a maximum number of players which take any credit for the assist can be set based on the implementation.

In the illustrated example in the data structure 400, player $B_1$ can be credited with an assist, and can thereby be awarded with half as much credit as player $B_2$ (e.g., one third and two thirds of the credit, respectively). This can result in player $B_2$ being credited with 64% (two thirds of 96% (100%–4%=96%) and player $B_1$ being credited with 32% (one third of the 96% distributed among all players credited) of the goal. As further illustrated, each of the players on the defending team can be debited with 9.6% (96%/10) in each of their defensive accounts. However, in some implementations, some level of fault for the goal can be calculated and/or assigned to each of the players on the defending team, such that each of the players are only debited with an amount that is appropriate/proportionate to their fault in allowing the goal to occur. In some aspects, each state 320 is considered from the point of view of the team that is currently in a possession of the ball.

As noted above, each of the actions 330 can signify a beginning and/or an end of one or more states 320. Depending on what the scoring probability of the last state 320 is, one or more of the players on each team can be credited/debited with at least a portion of this scoring probability at the end of the sporting event 300. For example, as further illustrated in the data structure 400 of FIG. 4, if team B has a 0.1% chance of scoring at the end of the game, then each of the players on team A can be credited with 0.01% in their defensive account and/or each of the players on team B can be debited with 0.01% in their offensive account. In some aspects, the player on team B which is in possession of the ball at the termination of the sporting event 300 can be debited with more of the probability (e.g., the full amount).

Although some of the calculations discussed herein are based on a probability of a team scoring based on an evaluation of a state 320, other probabilities and/or values assigned to a state 320 can additionally or alternatively be utilized. For example, as noted above, a value of/assigned to states 320 can be a mathematical expectation of the result (e.g., number of the points for the game expected from that state 320). In some implementations values of/assigned to states 320 can be abstract rating points, which may have little/no relation to the match result.

In some implementations, if a player dribbles the ball from a state 320 where their team has a 1% chance of scoring to a new position, then the dribbling action can be regarded as an action 330 which forms a new state 320. If, for example, the new state 320 provides a 3% chance of scoring, then the additional 2% difference between the states 320 can be credited to the offensive account of the player and or debited from one or more defensive accounts of the players of the opposing team (e.g., all players in the field of play or some portion thereof, which may be based on fault).

Any subset and/or combination of the data described with respect to FIGS. 3-9 can be stored, analyzed, transmitted, displayed, used for the purposes of assessing the relative skill of participants in sporting activities, and/or the like. For example, on a per-game and/or a per-season basis (and/or any smaller or larger scale), the numbers recorded within a player's offensive and/or defensive account (or some variation thereof) can be displayed for viewing by analysts, sports agents, fans, and/or the like. In another example, the numbers recorded within a player's offensive and/or defensive account (or some variation thereof) can be utilized to rank players with respect to other players in the same/similar skill level and/or across multiple skill levels (e.g., professional, semi-professional, collegiate, high school, and/or the like).

Figure 10:
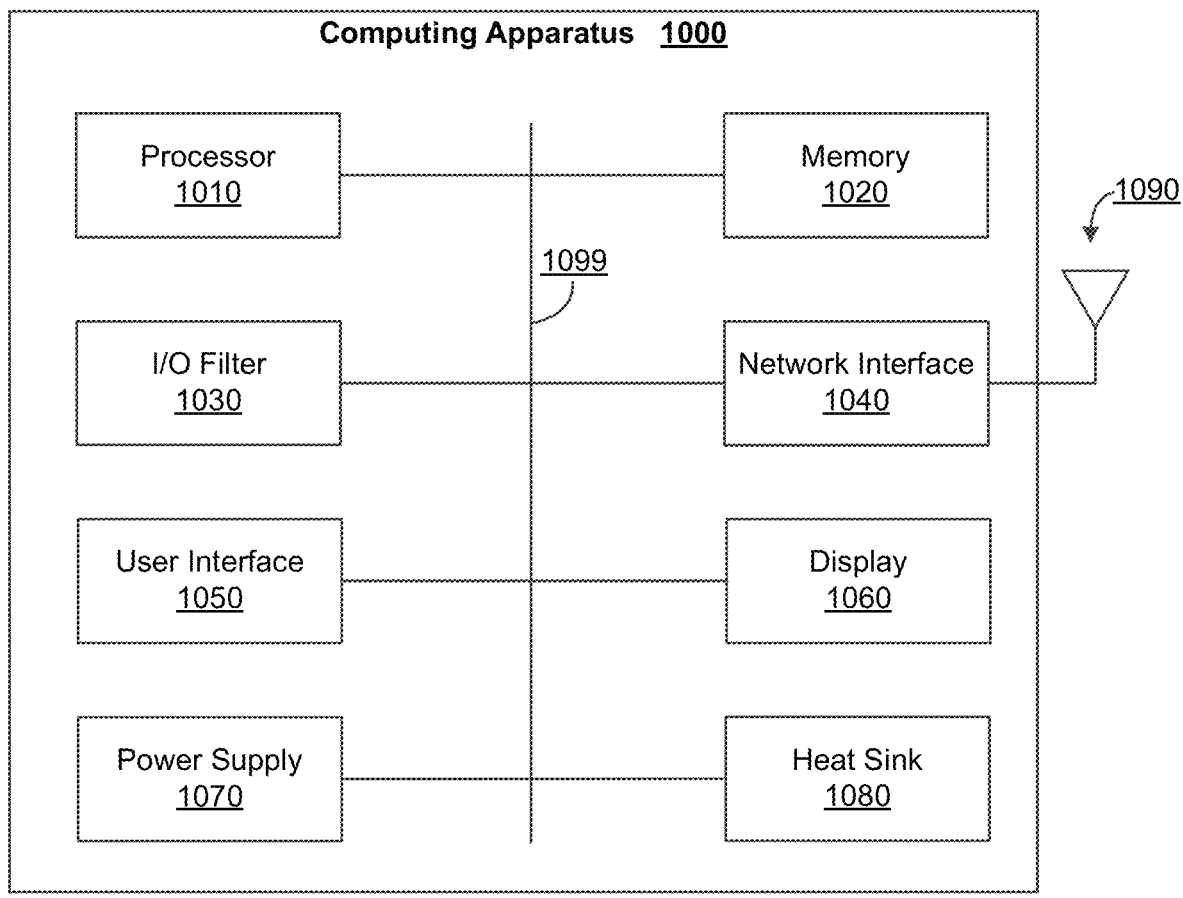
FIG. 10 depicts a block diagram of an example computing apparatus, in accordance with some example implementations.

FIG. 10 illustrates an example computing apparatus 1000 which may be used to implement one or more of the described devices and/or components, in accordance with some example implementations. For example, at least a portion of the computing apparatus 1000 may be used to implement at least a portion of the computing device 110, an apparatus providing the database 120, an apparatus providing the external software 130, the user access device 140, one or more of the sensor devices 150, the access device 165, the sensor device 250, one or more of the plurality of sensors 252, the controller 254, the user device 240, the server 210, and/or the like. Computing apparatus 1000 may perform one or more of the processes described herein.

As illustrated, computing apparatus 1000 may include one or more processors such as processor 1010 to execute instructions that may implement operations consistent with those described herein. Apparatus 1000 may include memory 1020 to store executable instructions and/or information. Memory 1020 may include solid-state memory, solid-state disk drives, magnetic disk drives, or any other information storage device. In some aspects, the memory 1020 may provide storage for at least a portion of a database (e.g., the database 120 or some other organization of data). Apparatus 1000 may include a network interface 1040 to a wired network or a wireless network, such as the network 160 of FIG. 1. Wireless networks may include WiFi, WiMax, and cellular networks (2G/3G/4G/5G), and/or any other wireless network. In order to effectuate wireless communications, the network interface 1040, for example, may utilize one or more antennas, such as antenna 1080.

Apparatus 1000 may include one or more user interface, such as user interface 1050. The user interface 1050 can include hardware or software interfaces, such as a keyboard, mouse, or other interface, some of which may include a touchscreen integrated with a display 1030. The display 1030 may be used to display information such as promotional offers or current inventory, provide prompts to a user, receive user input, and/or the like. In various implementations, the user interface 1050 can include one or more peripheral devices and/or the user interface 1050 may be configured to communicate with these peripheral devices.

In some aspects, the user interface 1050 may include one or more of the sensors described herein and/or may include an interface to one or more of the sensors described herein. The operation of these sensors may be controlled at least in part by a sensor module 1060. The apparatus 1000 may also comprise and input and output filter 1070, which can filter information received from the sensors or other user interfaces, received and/or transmitted by the network interface, and/or the like. For example, signals detected through sensors can be passed through the filter 1070 for proper signal conditioning, and the filtered data may then be passed to the microcontroller sensor module 1060 and/or processor 1010 for validation and processing (e.g., before transmitting results or an indication via the network interface 1040). The apparatus 1000 may be powered through the use of one or more power sources, such as power source 1090. As illustrated, one or more of the components of the apparatus 1000 may communicate and/or receive power through a system bus 1099.

FIG. 11 illustrates a flowchart of a method for tracking and/or analyzing participants in a sporting event, in accordance with some example implementations. In various implementations, the method 1100 (or at least a portion thereof) may be performed by one or more of the computing system 110, an apparatus providing the database 120, an apparatus providing the external software 130, a user access device 140, one or more of the sensor devices 150, the access device 165, the computing apparatus 1000, other related apparatuses, and/or some portion thereof. In some aspects, the apparatus 1000 may be regarded as a server.

Method 1100 can start at operational block 1110 where the apparatus 1000, for example, can receive, for each of a plurality of tracked participants of a sporting-activity, data (e.g., sensor data, imaging data, stored data, transmitted data, and/or the like) indicative of at least a position of each of the plurality of tracked participants. In some aspects, at least a portion of the data can come from a plurality of sensors deployed within an area of interest (e.g., an area of play). In some implementations, the plurality of sensors can comprise at least one of an accelerometer, a gyroscope, a geo-spatial sensor, a global positioning sensor, and/or the like. In some aspects, at least a portion of the data can come from one or more image/video capturing device and/or image/video processing (e.g., semi-autonomous).

Method 1100 can proceed to operational block 1120 where the apparatus 1000, for example, can calculate, based on the data, a first probability that one or more of the plurality of tracked participants will successfully complete a sporting outcome.

Method 1100 can proceed to operational block 1130 where the apparatus 1000, for example, can determine, based on the data, that an action occurred between at least two of the tracked participants. In some aspects, the action can include at least one of a pass, a shot, a steal, a foul, and/or the like. In some implementations, the at least two of the tracked participants can include a participant in possession of an object of interest and/or a participant who obtains possession of the object of interest. For example, the method 1100 can include identifying, based on the data, that the second participant has taken possession of the tracked object from a first participant, and/or identifying that the action comprises the second participant taking possession of the tracked object.

Method 1100 can proceed to operational block 1140 where the apparatus 1000, for example, can calculate, based on the data and in response to determining that the action occurred, a second probability that one or more of the plurality of tracked participants will successfully complete the sporting outcome.

Method 1100 can proceed to operational block 1150 where the apparatus 1000, for example, can assign, based on a difference between the first probability and the second probability, at least a portion of the difference to the at least two of the tracked participants.

In the event that the first participant is not on the same team as the second participant, the assigning can include assigning a negative value to an offensive account of the first participant (e.g., for losing the ball), wherein the negative value comprises at least a portion of a negative of the first probability. For example, if the first probability was 1%, then the offensive account of the first participant can be debited with −1% or something closer to zero (e.g., −0.01, −0.005, and/or the like).

Method 1100 can additionally or alternatively include identifying, based on the data, that a third participant is at least partially at fault for the action occurring. In such an embodiment, the first participant can be on the same team as the second participant and the third participant is not on the same team. Accordingly, assigning at least a portion of the difference can include assigning a positive value to an offensive account of the first participant, wherein the positive value comprises at least a portion of the difference. For example, if the first probability was 1% and the second probability was 3%, then the offensive account of the first participant can be credited with anything between zero and 2% (e.g., 0, +0.01, +0.02, and/or the like). Similarly, assigning at least a portion of the difference can include assigning a negative value to a defensive account of the third participant, wherein the negative value comprises at least a portion of a negative of the difference (e.g., anything between zero and −2%).

In some implementations, the method 1100 can include determining, based on the data, that the second participant successfully completed the sporting outcome, such as a goal scored on an opposing team. The method 1100 could further include assigning, based on a second difference between the second probability and a value of one, at least a portion of the second difference to an offensive account of the second participant. For example, if the second probability was 10%, then the offensive account of the second participant can be credited with the 90% difference (e.g., +0.9 or less). In some embodiments, the method can include assigning at least a portion of the second difference to an offensive account of the first participant, if the action comprising a pass from the first participant to the second participant. For example, if the second probability was 10%, then the offensive account of the first participant can be credited with some portion of the 90% difference (e.g., +0.45, +0.30, +0.15, and/or the like).

FIG. 12 illustrates a flowchart of another method for tracking and/or analyzing participants in a sporting event, in accordance with some example implementations. In various implementations, the method 1200 (or at least a portion thereof) may be performed by one or more of the computing system 110, an apparatus providing the database 120, an apparatus providing the external software 130, a user access device 140, one or more of the sensor devices 150, the access device 165, the computing apparatus 1000, other related apparatuses, and/or some portion thereof. In some aspects, the apparatus 1000 may be regarded as a server.

Method 1200 can start at operational block 1210 where the apparatus 1000, for example, can receive, for one or more of a plurality of tracked participants, first data (e.g., sensor data, imaging data, stored data, transmitted data, and/or the like) indicative of at least a position of each of the one or more of the plurality of tracked participants.

Method 1200 can proceed to operational block 1220 where the apparatus 1000, for example, can receive second data (e.g., sensor data, imaging data, stored data, transmitted data, and/or the like) indicative of at least a position of a tracked object. In some aspects, at least a portion of the first data and/or the second data can come from a plurality of sensors deployed within an area of interest (e.g., an area of play). In some implementations, the plurality of sensors can comprise at least one of an accelerometer, a gyroscope, a geo-spatial sensor, a global positioning sensor, and/or the like. In some aspects, at least a portion of the first data and/or the second data can come from one or more image/video capturing device and/or image/video processing (e.g., semi-autonomous).

Method 1200 can proceed to operational block 1230 where the apparatus 1000, for example, can determine, based on the first data and the second data, a first participant in possession of the tracked object.

Method 1200 can proceed to operational block 1240 where the apparatus 1000, for example, can calculate, based on the second data and historical data, a first probability that the first team (e.g., the team on which the first participant is a member) successfully completes a scoring action.

Method 1200 can proceed to operational block 1250 where the apparatus 1000, for example, can calculate, based on the first data and the second data, that a first action (e.g., a pass or steal) occurred between the first participant and a second participant.

Method 1200 can proceed to operational block 1260 where the apparatus 1000, for example, can calculate, based on the second data and in response to the first action, a second probability that a second team (e.g., the team on which the second participant is a member) successfully completes the scoring action. In some aspects, the first action can include at least one of a pass, a shot, a steal, a foul, and/or the like. In some aspects, the first participant and the second participant can be on the same team, meaning that the first team and the second team are the same team.

Method 1200 can proceed to operational block 1270 where the apparatus 1000, for example, can assign, based on a difference between the first probability and the second probability, at least a first portion of the difference to (e.g., to one or more data structures associated with) the first participant and/or the second participant.

Although several aspects are described herein with respect to soccer, the same and/or similar data structures can be adapted for use in monitoring other sports/activities. For example, the data structures described herein can be easily modified to track athletes/participants in basketball games, hockey games, lacrosse matches, polo matches, handball games (e.g., water polo), rugby matches, football games, volleyball games, and/or the like. With potentially more modification, the data structures described herein can additionally or alternatively be used to track athletes/participants in racquet/racket sport matches (e.g., tennis or squash), billiards, races (e.g., automobile, boat, cycle, animal, and/or the like), baseball games, cricket games, and/or the like. Although sensors may not be required, in some implementations, similar data structures and/or methodologies can be utilized to track the performance of video game players (e.g., professional gamers).

Although several aspects are described herein with respect to sensors deployed within an area of interest, other sensor, imaging, and/or tracking technologies can be leveraged. For example, cameras, filters, scanners, image/video processing (e.g., semi-autonomous, semi-automatic, etc.), and/or the like can be utilized to monitor and/or track participants and/or objects of interest in sporting activities. If such hardware and/or software is utilized, the underlying data structures (and/or some variation thereof) described herein can still be leveraged to track and/or analyze participants and objects. Similarly, the underlying data structures, evaluation techniques, and/or the like can be utilized in systems which obtain information through other means, such as stored and/or manually input data. Systems and methods which incorporate the techniques described herein can provide information on participants (e.g., athletes) which is not otherwise available through conventional analysis.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic input, speech input, tactile input, and/or the like. Other possible input devices include touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such phrases are intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." The use of the term "based on," above and in the claims is intended to mean "based at least in part on," such that a feature or element that is not recited is also permissible.

The illustrated methods are exemplary only. Although the methods are illustrated as having a specific operational flow, two or more operations may be combined into a single operation, a single operation may be performed in two or more separate operations, one or more of the illustrated operations may not be present in various implementations, and/or additional operations which are not illustrated may be part of the methods. Similarly, although separate methods may be illustrated and described, any method or portion thereof can be combined with one or more additional methods and/or portions thereof. In addition, the logic flows depicted in the accompanying figures and/or described herein do not necessarily require the particular order shown, or sequential order, to achieve desirable results. Other implementations may be within the scope of the following claims.

What is claimed is:

1. A system comprising:
   at least one processor; and
   at least one memory storing instructions which, when executed by the at least one processor, cause operations comprising:
      receiving, at a server, a first data and a second data from a plurality of wireless sensors deployed within an area of interest, wherein at least a first portion of the plurality of wireless sensors are mounted on a plurality of tracked participants and at least a second portion of a plurality of tracked objects are mounted on a tracked object, the plurality of wireless sensors each including a controller, wireless circuitry, and a global positioning system sensor to track location, wherein a distributed database including a list of data records is maintained among the plurality of wireless sensors using block chain techniques to exchange data and/or provide guarantees regarding the data;
      determining, by the server and based on the first data and the second data, a first probability of the tracked object entering a first scoring zone, the first data comprising information indicative of at least a location of one or more of the plurality of tracked participants of a sporting event, the plurality of tracked participants including a first participant on a first team and a second participant on a second team, the second data comprising information indicative of at least a location of the tracked object;
      determining, by the server and in response to detecting an action which at least changes the location of the tracked object and based on a new location of the tracked object, a second probability of the tracked object entering a second scoring zone, the action occurring between the first participant and the second participant;

assigning, by the server and based on a difference between the first probability and the second probability, at least a portion of the difference to the first participant and/or the second participant; and recording at least the portion of the difference to the first participant and/or the second participant in at least one of a first participant account and a second participant account, the first participant account and the second participant account further configured to accumulate probability differences based on an updated location of the tracked object.

2. The system of claim 1, wherein the plurality of wireless sensors further comprises at least one of an accelerometer, a gyroscope, a camera, and a geo-spatial sensor.

3. The system of claim 1, wherein the operations further comprise:

identifying, based on the first data and the second data, that the first participant is in possession of the tracked object; and identifying, based on the first data and the second data, that the second participant has taken possession of the tracked object, wherein the action comprises the second participant taking possession of the tracked object.

4. The system of claim 3, wherein the first participant is not on a same team as the second participant, the first participant account includes a first offensive account, and wherein assigning at least a portion of the difference comprises:

assigning a negative value to the first offensive account of the first participant.

5. The system of claim 3, wherein the operations further comprise:

identifying, based on the first data and the second data, that a third participant is at least partially at fault for the action occurring, wherein the first participant is on a same team as the second participant, the first team and the second team being the same team, wherein the third participant is not on the same team as the second participant, wherein the first participant account includes a first offensive account, and wherein assigning at least a portion of the difference comprises:

assigning a positive value to the first offensive account of the first participant, wherein the positive value comprises at least a portion of the difference; and assigning a negative value to a defensive account of the third participant.

6. The system of claim 1, wherein the first participant account includes a first offensive account, wherein the second participant account includes a second offensive account, and wherein the operations further comprise:

determining, based on the first data and the second data, that the second participant caused the tracked object to enter a second scoring zone; and assigning, based on a second difference between the second probability and a numerical value of one, at least a portion of the second difference to the second offensive account of the second participant.

7. The system of claim 6, wherein the operations further comprise:

assigning, in response to the action comprising a pass from the first participant to the second participant, at least a portion of the second difference to the first offensive account of the first participant.

8. The system of claim 1, wherein determining the first probability of the tracked object entering a first scoring zone and determining the second probability of the tracked object entering a second scoring zone is further based on a machine learning algorithm.

9. A method comprising:

receiving, at a server, a first data and a second data from a plurality of wireless sensors deployed within an area of interest, wherein at least a first portion of the plurality of wireless sensors are mounted on a plurality of tracked participants and at least a second portion of a plurality of wireless sensors are mounted on a tracked object, the plurality of wireless sensors each including a controller, wireless circuitry, and a global positioning system sensor to track location, wherein a distributed database including a list of data records is maintained among the plurality of wireless sensors using block chain techniques to exchange data and/or provide guarantees regarding the data;

determining, by the server and based on the first data and the second data, a first probability of the tracked object entering a first scoring zone, the first data comprising information indicative of at least a location of one or more of a plurality of tracked participants of a sporting event, the plurality of tracked participants including a first participant on a first team and a second participant on a second team, the second data comprising information indicative of at least a location of the tracked object;

determining, by the server and in response to detecting an action which at least changes the location of the tracked object and based on a new location of the tracked object, a second probability of tracked object entering a second scoring zone the action occurring between the first participant and the second participant;

assigning, by the server and based on a difference between the first probability and the second probability, at least a portion of the difference to the first participant and/or the second participant; and recording at least the portion of the difference to the first participant and/or the second participant in at least one of a first participant account and a second participant account, the first participant account and the second participant account further configured to accumulate probability differences based on an updated location of the tracked object.

10. The method of claim 9, wherein the plurality of wireless sensors further comprises at least one of an accelerometer, a gyroscope, a camera, and a geo-spatial sensor.

11. The method of claim 9, further comprising:

identifying, based on the first data and the second data, that the first participant is in possession of the tracked object; and identifying, based on the first data and the second data, that the second participant has taken possession of the tracked object, wherein the action comprises the second participant taking possession of the tracked object.

12. The method of claim 11, wherein the first participant is not on a same team as the second participant, the first participant account includes a first offensive account, and wherein assigning at least a portion of the difference comprises:

assigning a negative value to the first offensive account of the first participant.

13. The method of claim 11, further comprising:

identifying, based on the first data and the second data, that a third participant is at least partially at fault for the action occurring, wherein the first participant is on a same team as the second participant, the first team and the second team being the same team, wherein the third participant is not on the same team as the second participant, wherein the first participant account includes a first offensive account, and wherein assigning at least a portion of the difference comprises:
assigning a positive value to the first offensive account of the first participant, wherein the positive value comprises at least a portion of the difference; and
assigning a negative value to a defensive account of the third participant.

14. The method of claim 9, wherein the first participant account includes a first offensive account, wherein the second participant account includes a second offensive account, and further comprising:
determining, based on the first data and the second data, that the second participant caused the tracked object to enter a second scoring zone;
assigning, based on a second difference between the second probability and a numerical value of one, at least a portion of the second difference to the second offensive account of the second participant; and
assigning, in response to the action comprising a pass from the first participant to the second participant, at least a portion of the second difference to the first offensive account of the first participant.

15. A non-transitory computer-readable medium comprising instructions which, when executed by at least one processor, cause operations comprising:
receiving, at a server, a first data and a second data from a plurality of wireless sensors deployed within an area of interest, wherein at least a first portion of a plurality of wireless sensors are mounted on a plurality of tracked participants and at least a second portion of the plurality of wireless sensors are mounted on a tracked object, the plurality of wireless sensors each including a controller, wireless circuitry, and a global positioning system sensor to track location, wherein a distributed database including a list of data records is maintained among the plurality of wireless sensors using block chain techniques to exchange data and/or provide guarantees regarding the data;
determining, by the server and based on the first data and the second data, a first probability of the tracked object entering a first scoring zone, the first data comprising information indicative of at least a location of one or more of a plurality of tracked participants of a sporting event, the plurality of tracked participants including a first participant on a first team and a second participant on a second team, the second data comprising information indicative of at least a location of the tracked object;
determining, by the server and in response to detecting an action which at least changes the location of the tracked object and based on a new location of the tracked object, a second probability of the tracked object entering a second scoring zone, the action occurring between the first participant and the second participant;
assigning, by the server and based on a difference between the first probability and the second probability, at least a portion of the difference to the first participant and/or the second participant; and
recording at least the portion of the difference to the first participant and/or the second participant in at least one of a first participant account and a second participant account, the first participant account and the second participant account further configured to accumulate probability differences based on an updated location of the tracked object.

16. The non-transitory computer-readable medium of claim 15, wherein the plurality of wireless sensors further comprises at least one of an accelerometer, a gyroscope, a geo-spatial sensor.

17. The non-transitory computer-readable medium of claim 15, wherein the operations further comprise:
identifying, based on the first data and the second data, that the first participant is in possession of the tracked object; and
identifying, based on the first data and the second data, that the second participant has taken possession of the tracked object, wherein the action comprises the second participant taking possession of the tracked object.

18. The non-transitory computer-readable medium of claim 17, wherein the first participant is not on a same team as the second participant, the first participant account includes a first offensive account, and wherein assigning at least a portion of the difference comprises:
assigning a negative value to the first offensive account of the first participant.

* * * * *